(12) United States Patent
Holmstrom et al.

(10) Patent No.: US 8,929,982 B2
(45) Date of Patent: Jan. 6, 2015

(54) ISCHEMIA DETECTION (71) Applicant: St. Jude Medical AB, Jarfalla (SE)

(72) Inventors: Nils Holmstrom, Jarfalla (SE); Michael Broome, Ekero (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/653,276

(22) Filed: Oct. 16, 2012

(65) Prior Publication Data

US 2013/0110187 A1    May 2, 2013

(30) Foreign Application Priority Data

Oct. 27, 2011  (EP) .................................. 11186923

(51) Int. Cl.
| $A61N\ 1/365$ | (2006.01) |
| $A61B\ 5/145$ | (2006.01) |
| $A61N\ 1/37$ | (2006.01) |
| $A61B\ 5/1459$ | (2006.01) |
| $A61B\ 5/1473$ | (2006.01) |

(52) U.S. Cl.
CPC ........ $A61B\ 5/14542$ (2013.01); $A61N\ 1/36557$ (2013.01); $A61N\ 1/3702$ (2013.01); $A61B\ 5/1459$ (2013.01); $A61B\ 5/1473$ (2013.01)
USPC .......................................................... 607/22

(58) Field of Classification Search
USPC ........... 607/22–24, 17, 18; 600/508, 510, 513
See application file for complete search history.

(56) References Cited

U.S. PATENT DOCUMENTS 7,389,142 B2 *   6/2008   Holmstrom .................... 607/18

\* cited by examiner

*Primary Examiner* — George Evanisko (57) ABSTRACT

An implantable medical device comprises a connector connectable to an implantable oxygen sensor configured to generate a sensor signal representative of oxygen concentration in coronary sinus blood in a subject's heart. An ischemia detector is connected to the connector and configured to detect an ischemic event in the heart if the sensor signal indicates a temporary decrease in oxygen concentration in the coronary sinus blood below a normal level followed by a temporary increase in oxygen concentration in the coronary sinus blood above the normal level.

9 Claims, 4 Drawing Sheets

ISCHEMIA DETECTION

CROSS REFERENCE TO RELATED APPLICATIONS

This application claims the benefit of U.S. Provisional Application Ser. No. 61/558,022, filed Nov. 10, 2011, entitled Ischemia Detection, and European Patent Application EP 11186923.6, filed Oct. 27, 2011.

TECHNICAL FIELD

The embodiments generally relate to ischemia detection, and in particular such ischemia detection performed based on oxygen concentration in coronary sinus blood.

BACKGROUND

Ischemia is the lack of oxygen supply to cells. In animals, including humans, the underlying cause of ischemia is typically a cardiovascular disease, where blood vessels may be affected by atherosclerosis. Cardiac ischemia is caused by restriction of blood flow in the coronary arteries, e.g. due to atherosclerosis. This reduced blood flow and the resulting lack of oxygen to the myocytes in the heart may lead to several effects, including contractile dysfunction and hibernating cells. These various effects may in turn decrease the hemodynamic performance of the heart, which ultimately can result in worsening heart failure and further decrease in pumping capacity.

Ischemic heart disease (IHD) is very common. IHD may be symptomatic, such as in angina pectoris, causing the patient to experience severe discomfort and pain. However, a majority of ischemic periods are silent and therefore hard to detect and classify. Most ischemic episodes, regardless of being symptomatic or silent, are reversible but still influence the risk of arrhythmias, the functional state and long-term remodeling of the heart.

A common technique in the art to detect cardiac ischemia is to measure oxygen saturation ($SO_2$) in coronary sinus blood, such as disclosed in U.S. Pat. Nos. 5,156,148; 5,199, 428; US 2005/0154370; US 2008/0177194 and EP 1 386 637. These prior art documents generally state that cardiac ischemia is detected as a decrease in $SO_2$ in the coronary sinus blood.

Prior art techniques that perform ischemia detection based solely on a reduction in $SO_2$ in coronary sinus blood run a risk of classifying non-ischemic events as cardiac ischemia. Hence, there is a need for a more accurate cardiac ischemia detection.

SUMMARY

An aspect of the embodiments defines an implantable medical device comprising a connector connectable to an implantable oxygen sensor configured to generate a sensor signal representative of oxygen concentration in coronary sinus blood of a subject's heart. The sensor signal is processed by an ischemia detector connected to the connector. The ischemia detector is configured to detect an ischemic event in the heart if the sensor signal indicates a temporary decrease in oxygen concentration in the coronary sinus blood below a normal oxygen concentration level followed by an increase in oxygen concentration in the coronary sinus blood above the normal oxygen concentration level.

Another aspect of the embodiments defines a method of detecting an ischemic event in a subject's heart. The method comprises measuring oxygen concentration in coronary sinus blood of the heart and detecting an ischemic event if the measured oxygen concentration in the coronary sinus blood temporarily decreases below a normal oxygen concentration level followed by an increase in measured oxygen concentration in the coronary sinus blood above the normal oxygen concentration level.

The embodiments provide accurate ischemia detection and are capable of discriminating between true ischemic episodes and non-ischemic episodes, such as periods of heavy exercise, which could be incorrectly interpreted as ischemic episodes if the detection is based solely on a drop in oxygen concentration in coronary sinus blood. However, the true ischemic episodes are detected by the embodiments as an increase in oxygen concentration in coronary sinus blood following the initial drop in oxygen concentration. This subsequent increase in oxygen concentration above the normal or baseline concentration is not present during non-ischemic events.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The embodiments generally relate to ischemia detection, and in particular such ischemia detection performed based on oxygen concentration in coronary sinus blood.

The ischemia detection of the embodiments is accurate in detecting ischemic events and in particular temporary or reversible ischemic events in a subject's heart, preferably a mammalian subject and in particular a human subject. A temporary ischemic event or episode implies that there is a mismatch between the supply of oxygen and other blood-borne substances needed by the myocytes and the demands of the myocytes for these substances. Such temporary ischemic events can, for instance, occur when the perfusion in a portion of the heart is hindered or at least severely restricted for some seconds or minutes. This means that the flow of arterial blood to the heart portion will not be sufficient to maintain sufficient levels of oxygen and other blood-borne substances needed by the myocytes, hence ischemia occurs. The temporary obstruction or restriction of the blood flow then ceases and/or the demands decrease so that supply-demand balance is resumed.

The embodiments are able to accurately detect such temporary ischemic events and discriminate them from other non-ischemic events that may cause a temporary reduction in oxygen concentration in a portion of the heart, such as during exercise or increased workload of the subject.

This means that if ischemia detection is based solely on a reduction in blood oxygen concentration as in the prior art documents mentioned herein, flawed ischemia detection may occur by incorrectly classifying a non-ischemic event, such as during exercise, as a true temporary ischemic event.

The ischemia detection of the embodiments is based on an implantable oxygen sensor that is configured to monitor the oxygen concentration in coronary sinus blood of a subject's heart. A particular processing of the sensor signal from the implantable oxygen sensor is applied to detect ischemic episodes and discriminate such ischemic episodes from non-ischemic events.

Figure 1:
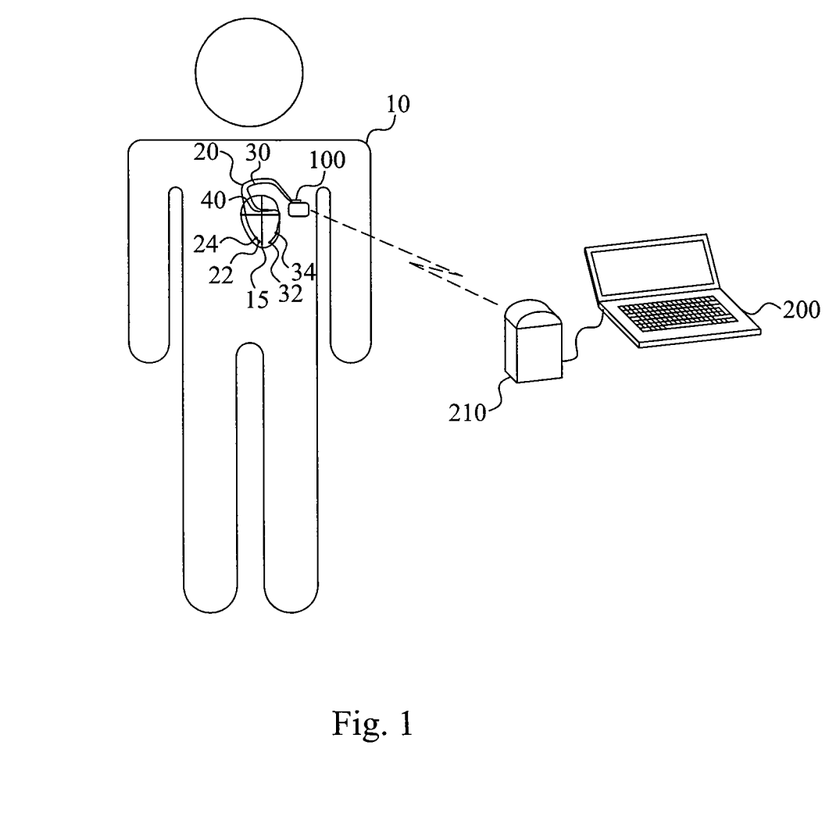
FIG. 1 is a schematic overview of a human subject equipped with an implantable medical device according to an embodiment.

FIG. 1 is a schematic overview of a subject, represented by a human subject 10 having an implantable medical device (IMD) 100 according to the embodiments. The IMD 100 is implanted in the subject 10 in order to detect ischemic episodes in the subject's heart 15. The IMD 100 can, in addition, be employed to provide cardiac therapy and/or monitoring, such as to provide pacing therapy to the subject's heart 15. In such a case, the IMD 100 can be in form of a pacemaker or an implantable cardioverter-defibrillator (ICD). The IMD 100 is, however, not limited to such device implementations but can indeed be an implantable ischemia detecting device or be any implantable medical device that is equipped with an ischemia detecting functionality as disclosed herein.

The IMD 100 is in operation connected to an implantable oxygen sensor 40 that monitors the oxygen concentration in coronary sinus blood. The implantable oxygen sensor 40 is typically arranged on an implantable medical lead 30 or catheter that is connected to the IMD 100 and runs therefrom up to the implementation site of the implantable oxygen sensor 40, such as in the coronary sinus (coronary venous system), e.g. in a left lateral vein or postero-lateral vein.

The implantable medical lead 30 could be a dedicated sensor-carrying lead or catheter. Alternatively, the implantable medical lead 30 not only carries the implantable oxygen sensor 40 but is also used by the IMD 100 for providing cardiac therapy and/or monitoring. For instance, the implantable medical lead 30 could be a left ventricular (LV) cardiac lead 30 having at least one electrode 32, 34, typically denoted pacing and sensing electrode 32, 34 in the art. In such a case, the IMD 100 is able to deliver pacing pulses to the left ventricle of the heart 15 and sense electrical activity from the left ventricle via the electrode(s) 32, 34 of the LV cardiac lead 30. As is well known in the art, an LV cardiac lead 30 is generally implanted via the coronary sinus venous system. Hence, the LV cardiac lead 30 is therefore highly suitable to carry or at least be connected to the implantable oxygen sensor 40 to position the sensor 40 for enabling monitoring oxygen concentration in coronary sinus blood.

The implantable oxygen sensor 40 is preferably arranged on the implantable medical lead 30 to be positioned in the main stem of the coronary sinus when implanted in the body of the subject 10. At that position in the coronary sinus the implantable oxygen sensor 40 is able to monitor the blood from the entire coronary circulation and almost the entire myocardium will be monitored.

The IMD 100 can also be connected to other cardiac leads, for instance a right ventricular (RV) cardiac lead 20 and/or an atrial cardiac lead (not illustrated). An RV cardiac lead 20 is typically provided inside the right ventricle of the heart 15 and comprises one or more electrodes 22, 24 that can be used by the IMD 100 to apply pacing pulses to the right ventricle and/or sense electrical activity from the right ventricle. An atrial cardiac lead, typically a right atrial (RA) cardiac lead having at least one electrode arranged in or in connection with the right atrium, can be used by the IMD 100 in order to provide atrial pacing and/or sensing. Instead of or as a complement to an RA cardiac lead, the IMD 100 can be connected to a left atrial (LA) cardiac lead.

FIG. 1 additionally illustrates a non-implantable data processing device 200, such as in the form of a programmer, a home monitoring device, a hand-held or portable device, or a physician's workstation. The data processing device 200 comprises or is connected to a communication module or device 210 that is capable of wirelessly communicating with the IMD 100, preferably through radio frequency (RF) based communication or inductive telemetry. The data processing device 200 can then use the communication module 210 in order to interrogate the IMD 100 for diagnostic data recorded by the IMD 100 employing the electrodes 22, 24, 32, 34 of the connected cardiac lead(s) 20, 30 and the implantable oxygen sensor 40. Furthermore, the data processing device 200 can be used to program the IMD 100, such as by setting one or more programmable pacing parameters. According to the present embodiments, the IMD 100 can in particular be used to transmit notifications of detected ischemic episodes to the data processing device 200 for display to the subject 10 or the subject's physician. In addition, or alternatively, the IMD 100 could generate alarm messages in connection with the detection of a true ischemic episode to the data processing device 200 to alert the subject 10 or his/her physician.

The communication module 210 and the data processing device 200 can be separate devices as illustrated in FIG. 1, either wired connected or using a wireless connection, such as Bluetooth®, an infrared (IR) connection or an RF connection. In an alternative embodiment, the functionality and equipment of the communication module 210 can be housed within the data processing device 200.

In a general aspect of the embodiments the implantable medical device comprises a connector that is connectable to an implantable oxygen sensor. The implantable oxygen sensor is configured to generate a sensor signal that is representative of oxygen concentration in coronary sinus blood of a subject's heart. The implantable medical device also comprises an ischemia detector connected to the connector and configured to process the sensor signal received from the implantable oxygen sensor through the connector. The ischemia detector is configured to detect an ischemic event or episode in the heart if the sensor signal indicates a temporary decrease in oxygen concentration in the coronary sinus blood below a normal oxygen concentration in coronary sinus blood for a non-ischemic status of the heart followed by an increase in oxygen concentration in the coronary sinus blood above the normal oxygen concentration.

Thus, the implantable medical device detects the ischemic event based on an initial drop in oxygen concentration in coronary sinus blood below the normal, reference or baseline oxygen level representing a healthy, non-ischemic status. If this initial drop in oxygen concentration is then followed by an increase in oxygen concentration in coronary sinus blood above the normal oxygen level the ischemia detector concludes that the heart has suffered a temporary ischemic event or episode.

The present embodiments thereby differentiate from the prior art that performs the ischemia detection solely based on the drop in oxygen concentration in coronary sinus blood. Such a drop in oxygen concentration can, however, also occur during exercise and high activity levels of the subject. However, with a true ischemic episode the oxygen concentration does not only climb back to the normal or reference oxygen level but actually, temporarily, increases above this normal oxygen level before it subsequently returns back to the normal oxygen level. No such increase in oxygen concentration above the normal oxygen level is, though, seen following non-ischemic events, such as during exercise.

In other words during a temporary ischemic episode the perfusion in a heart portion will be hindered for some seconds or minutes. At this time no venous blood will come out from this heart portion and, thus, no change of oxygen concentration in the coronary sinus blood will occur. However, when the perfusion is established again the blood vessels will be highly dilated by intrinsic metabolic autoregulation, which will have the following impact on the coronary sinus blood. First a reduction of the oxygen concentration will take place due to the low oxygen content coming from the previously ischemic heart portion. Thereafter, the oxygen concentration will increase above the normal value due to the dilated coronary vessels and high reperfusion rate (coronary reperfusion hyperemia). After some more minutes the oxygen concentration will stabilize at a normal level. The increase in oxygen concentration after the temporary reduction in oxygen concentration generally takes place directly following the reduction in oxygen concentration. This means that the oxygen concentration typically goes directly from a minimum up to a maximum without any significant plateau at normal level.

The present embodiments can be used in connection with any implantable sensor that is capable of monitoring the oxygen concentration in coronary sinus blood. The implantable oxygen sensor does not necessarily have to be able to produce a sensor signal that represents an absolute oxygen concentration value. It is sufficient if the implantable oxygen sensor can be used to monitor variations of the oxygen concentration and thereby produce a sensor signal that represents relative oxygen concentration values.

There are various implantable oxygen sensors disclosed in the art and that can be used according to the embodiments. For instance, the implantable oxygen sensor can be a partial oxygen pressure ($pO_2$) sensor, such as an electrochemical $pO_2$ sensor, or a sensor that measures oxygen saturation ($SO_2$), such as an optical $SO_2$ sensor, or indeed any other type of implantable sensor that outputs a sensor signal that represents variations of oxygen concentration in venous blood in the coronary venous system.

In an embodiment, the implantable oxygen sensor could use a measurement sampling frequency to generate an oxygen concentration sample every heart beat, or multiple such samples per heart beat. Also a low sampling frequency could be used, such as every second heart beat or even lower. Instead of basing the sampling frequency on the heart rate, the implantable oxygen sensor could generate a measurement sample once every 0.1-10 seconds as illustrative but non-limiting examples.

Figure 2:
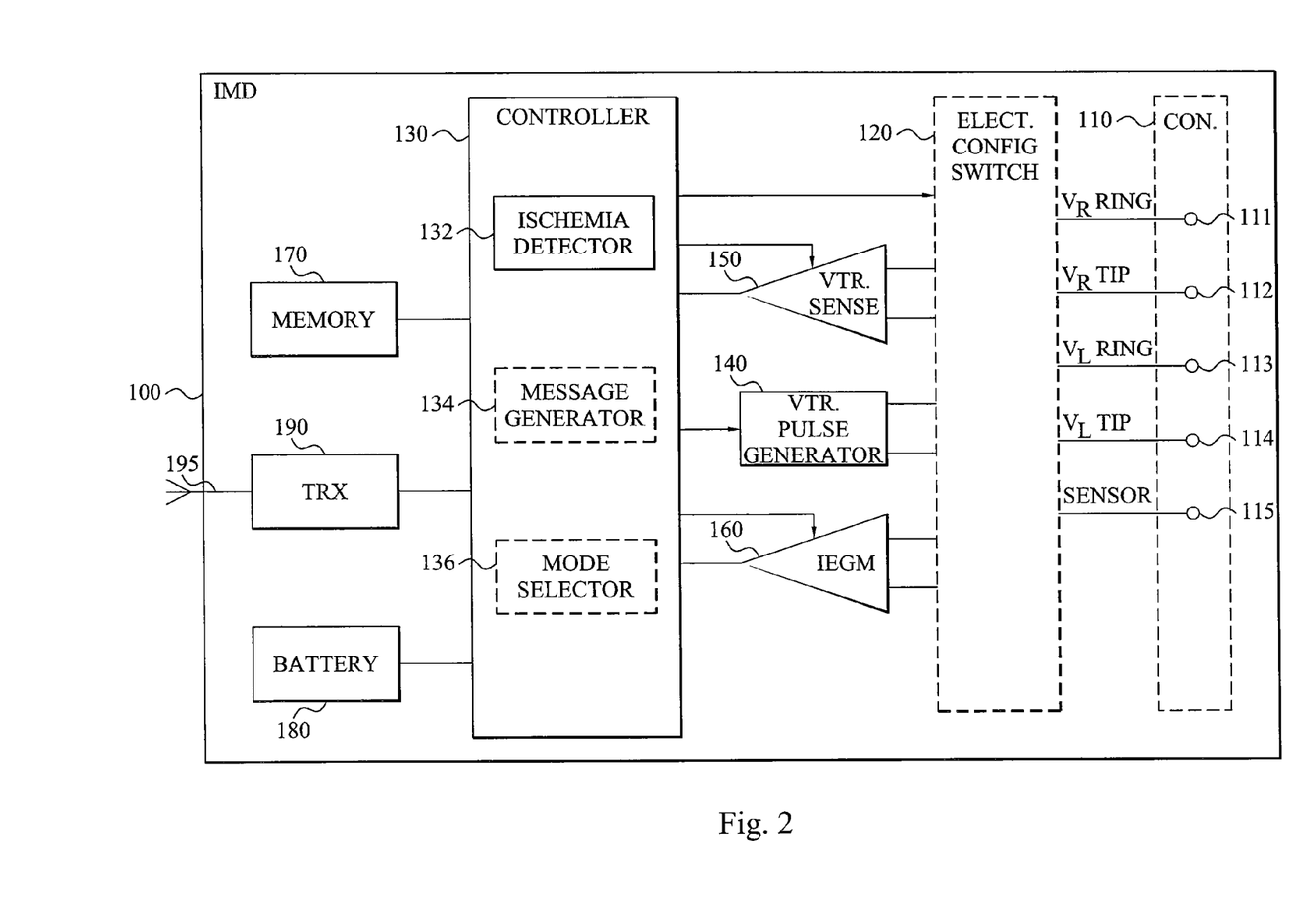
FIG. 2 is a schematic block diagram of an implantable medical device (IMD) according to an embodiment.

FIG. 2 is a schematic block diagram of an embodiment of an IMD 100 according to the embodiments. The IMD 100 illustrated in FIG. 2 corresponds to the IMD 100 shown in FIG. 1 and being connectable to an LV cardiac lead 30 and an RV cardiac lead 20.

The IMD 100 comprises a connector 110 having at least one connector terminal 115 configured to be connected to the implantable oxygen sensor 40. The connector 110 may also comprise connector terminals 111-114 configured to be connected to matching electrode terminals of one or more cardiac leads. With reference to FIGS. 1 and 2, in the particular shown example, the connector 110 comprises two connector terminals 113, 114, each of which is electrically connectable to a respective electrode terminal of the LV cardiac lead 30 and the tip electrode 32 and ring electrode 34 of the LV cardiac lead 30. In this example, the connector 110 also comprises connector terminals 111, 112 for electrical connection to the tip electrode 22 and ring electrode 24 of the RV cardiac lead 20. If the IMD 100 is also to be connectable to an atrial cardiac lead the connector 110 comprises one or more connector terminals to be connected to that atrial cardiac lead. Correspondingly, if the IMD 100 is only used in connection with an implantable oxygen sensor or the implantable oxygen sensor and the LV cardiac lead, the connector terminals 111-114 or 111-112 could be omitted, respectively.

FIG. 2 also illustrates the previously mentioned ischemia detector 132 that is connected to the connector 110, possibly through an optional electronic configuration switch 120. The ischemia detector 132 processes the sensor signal received from the implantable oxygen sensor for the purpose of detecting an ischemic event in the heart based on the sensor signal. Thus, the ischemia detector 132 compares the signal samples of the sensor signal in order to detect a temporary decrease in oxygen concentration in coronary sinus blood below normal oxygen concentration and any following increase in oxygen concentration above the normal oxygen concentration.

Figure 3:
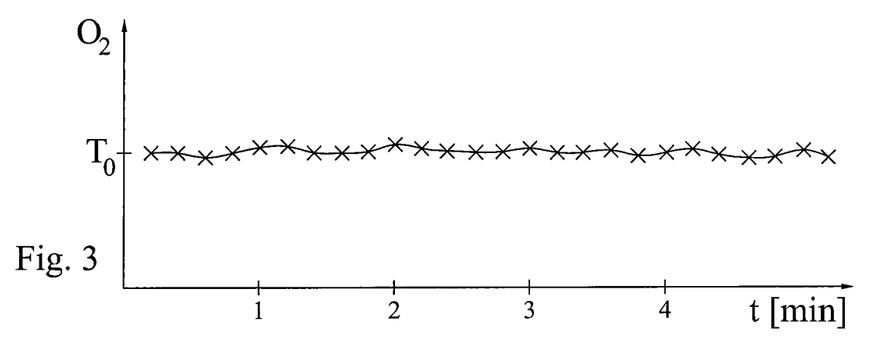
FIG. 3 is a diagram illustrating oxygen concentration in coronary sinus blood during a normal, non-ischemic state for a subject's heart.
Figure 4:
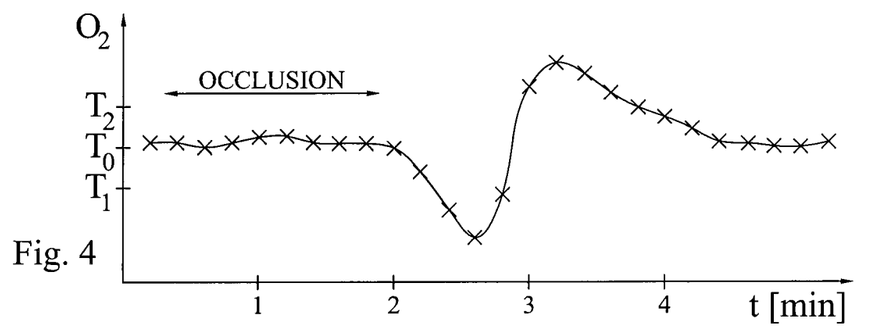
FIG. 4 is a diagram illustrating oxygen concentration in coronary sinus blood following an occlusion causing an ischemic event for a subject's heart.
Figure 5:
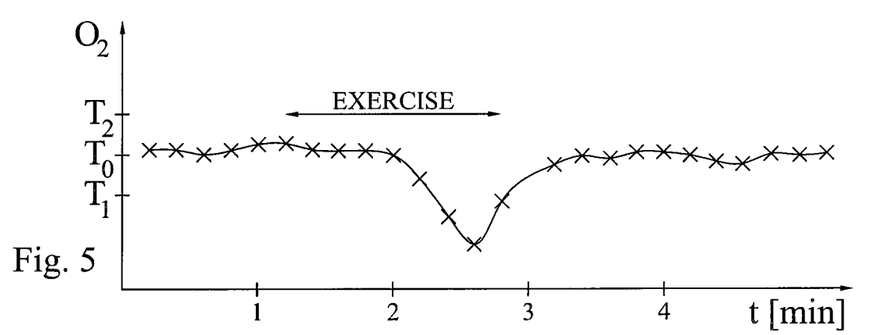
FIG. 5 is a diagram illustrating oxygen concentration in coronary sinus blood during a false, non-ischemic event for a subject's heart.

FIGS. 3-5 illustrate this concept. In FIG. 3 the sensor signal for a healthy non-ischemic heart is shown. As is seen in the diagram the oxygen concentration in coronary sinus blood varies relatively little due to the efficient autoregulation responding to metabolic needs of the myocytes in the heart. The monitored oxygen concentration is therefore relatively stable around the normal or baseline oxygen concentration, represented by the threshold concentration or level $T_0$ in FIGS. 3-5.

However in FIG. 4 a temporary occlusion in one or more blood vessels induces a temporary ischemic episode. As disclosed in the foregoing, with such an occlusion no venous blood will come out from the ischemic area and there is generally no significant change in the oxygen concentration in the coronary sinus blood. Once the occlusion is no longer present and perfusion is established again the blood vessels will be highly dilated by the intrinsic metabolic autoregulation, which causes an initial reduction of the oxygen concentration below the normal concentration $T_0$. This drop and decrease in oxygen concentration in the coronary sinus blood is generally temporary and limited in time and typically only occurs for no more than a few minutes, i.e. no more than 3-5 minutes. It could also be possible that the drop in oxygen concentration only occurs for no more than one minute. The initial short decrease in blood concentration below the normal concentration $T_0$ is followed by a temporary increase in oxygen concentration in coronary sinus blood above the normal concentration $T_0$. This increase in oxygen concentration generally lasts somewhat longer than the initial drop. In a typical case, the increase could continue for about one to five, such as two to five minutes before the oxygen concentration has returned back to the normal level. As is seen in FIG. 4, the increase in oxygen concentration in coronary sinus blood occurs directly following the temporary decrease in oxygen concentration, i.e. without any intermediate plateau at the normal level. Thereafter the oxygen concentration returns back to the normal level. Thus, following the temporary decrease and increase in oxygen concentration the oxygen concentration in coronary sinus blood will be substantially equal to the normal concentration level. Substantially equal generally corresponds in an embodiment to be equal to the normal concentration level $T_0 \pm 5\%$, preferably $T_0 \pm 2.5\%$ FIG. 5 illustrates the sensor signal in connection with a non-ischemic event, such as heavy exercise. The rather heavy workload and activity of the subject will in this case cause a temporary reduction in oxygen concentration due to the increase in metabolic need of the myocytes. The effective autoregulation will, however, soon lead to a return of the oxygen concentration and stabilization at the normal concentration $T_0$.

The ischemia detector 132 could use different threshold values $T_0$, $T_1$ and $T_2$ in the detection of ischemic events. In such a case, the initial drop in oxygen concentration of coronary sinus blood could be identified if the monitored oxygen concentration falls below a first threshold value $T_1$. A true ischemic event could then be discriminated from a non-ischemic event by investigating whether the oxygen concentration subsequently exceeds a second threshold value $T_2$, i.e. is a true ischemic event, or does not increase above this second threshold value, i.e. is a non-ischemic event. In this case $T_1 < T_0 < T_2$, with $T_0$ representing normal oxygen concentration as previously mentioned herein. In a particular embodiment $T_1 = T_0 - \Delta_1$ and $T_2 = T_0 + \Delta_2$, wherein $\Delta_1$, $\Delta_2$ represent defined hysteresis values. The values of these thresholds $T_0$, $T_1$ and $T_2$ or $T_0$ and $\Delta_1$, $\Delta_2$ can be stored in a memory 170 of the IMD 100 accessible to the ischemia detector 132. Non-limiting examples of the parameters $\Delta_1$, $\Delta_2$ is 10-15% of the threshold $T_0$. The two parameters $\Delta_1$, $\Delta_2$ can be equal or different.

The ischemia detector 132 can advantageously use detection windows in connection with monitoring the oxygen concentration. Thus, detection of an oxygen concentration in coronary sinus blood below the threshold $T_1$ could trigger the start of a first detection window. During this first detection window the ischemia detector 132 continues to process the sensor signal from the implantable oxygen sensor in order to detect any increase in the oxygen concentration above the threshold $T_2$. If no such an increase in oxygen concentration above the threshold $T_2$ is detected by the ischemia detector 132 before the first detection window has expired then the current event is not regarded as a true ischemic event. The length of the first detection window can be as previously mentioned, such as up to about 3-5 minutes.

Correspondingly a second detection window can be started once the ischemia detector 132 detects that the current oxygen concentration in coronary sinus blood exceeds the threshold $T_2$. During this second detection window the ischemia detector 132 continues to process the sensor signal from the implantable oxygen sensor in order to verify that the oxygen concentration decreases back to the normal oxygen concentration level. The second detection window could have a length of up to about 5 minutes.

In a particular embodiment, the ischemia detector 132 calculates an average oxygen concentration and compares this average oxygen concentration to the threshold values. The average oxygen concentration could then be an average of the sensor samples obtained from the implantable oxygen sensor during a defined time period, such as 1-10 s, or for a defined number of consecutive sensor samples, such as 5-10 samples.

Alternatively, multiple consecutive sensor samples are compared to a given threshold value and the oxygen concentration in coronary sinus blood is then regarded as being above or below the concentration level represented by the threshold value if all or at least a defined minimum of these multiple consecutive sensor samples exceed or are below the threshold value.

The above described techniques will combat or compensate for any noise in the sensor signal and furthermore represses the influence of any odd sensor sample that differs significantly from other sensor samples and is due to some other effect not related to the actual oxygen concentration in the coronary sinus blood.

The threshold values can be set by the subject's physician and downloaded to the IMD 100 using the data processing device shown in FIG. 1. The IMD 100 then comprises a transceiver (TX/RX) 190, see FIG. 2, having communication functionality for transmitting data to and receiving data from the data processing device. The transceiver 190 can be implemented as a single unit having both transmitting functionality and receiving functionality. In an alternative approach, the transceiver is replaced by one or more transmitters and one or more receivers. The transceiver (or transmitter and receiver) is connected to an antenna 195 to affect the communication. The antenna 195 could be an RF antenna or an inductive antenna, as illustrative examples.

The ischemia detector 132 generates, in an embodiment, a notification of each ischemic event that it detects based on the sensor signal. Such a notification could be a simple indication that an ischemic event has been detected. In alternative embodiments, the ischemia detector 132 additionally logs the current time when the ischemic event was detected. This information can then be entered in the memory 170 of the IMD 100. The ischemia detector 132 may additionally provide more detailed information of the ischemic event, such as the minimum oxygen concentration measured during the temporary drop in oxygen concentration, the duration of the drop in oxygen concentration (can be expressed in time units or in the number of signal samples for which the sample values, i.e. oxygen concentration, is below the first threshold $T_1$), the maximum oxygen concentration measured during the following temporary increase in oxygen concentration and/or the duration of the increase in oxygen concentration (can be expressed in time units or in the number of signal samples for which the sample values, i.e. oxygen concentration, is above the second threshold $T_2$).

The IMD 100 could then comprise a message generator 134 configured to generate a notification message comprising the notification of the detected ischemic event and optionally any additional information of the ischemic event as mentioned above. The message generator 134 could be configured to generate the notification message in response to the ischemia detector 132 detecting the ischemic event, i.e. basically generating the notification directly following the ischemia detection. The notification message could then be regarded as an alarm message that will inform the subject or the subject's physician in real time of any ischemic periods. The notification message is then wirelessly transmitted by the transceiver 190 to the data processing device (see FIG. 1). If the data processing device is in the form of a home monitoring device or a hand-held device carried by the subject, the device will inform the subject of the immediate ischemic event. This information can be used by the subject to, for instance, contact his/her physician and/or guide the subject in optimizing drug administration and titration. The information could also be of value for the subject to optimize his/her lifestyle in general to avoid episodes of ischemia.

The IMD 100 could alternatively store the notifications and any additional information descriptive of the detected ischemic events in the memory 170 to form a register of the subject's ischemia burden. The collected information is then uploaded when the patient visits his/her physician and is used as diagnostic information and/or for determination of optimal drug titration or device settings for the subject.

In a particular embodiment, the ischemia detector 132 is also configured to detect a false ischemic or non-ischemic event based on the sensor signal. In such a case, the ischemia detector 132 detects and classifies an event as representing a non-ischemic status of the heart if the sensor signal indicates a temporary decrease in oxygen concentration in the coronary sinus blood below the normal concentration followed by an increase in oxygen concentration back to the normal oxygen concentration but not significantly above the normal oxygen concentration (see FIG. 5). Also information of such non-ischemic events could be logged by the ischemia detector 132 in the memory 170.

In addition to or as a complement to generating notifications of detected ischemic and optionally non-ischemic events, the IMD 100 could initiate cardiac therapy to combat or compensate for the ischemic event. The IMD 100 then comprises a pulse generator 140, represented by a ventricular pulse generator 140 in FIG. 2. The pulse generator 140 is connected to the connector 110, optionally through the electronic configuration switch 120. The pulse generator 140 is configured to generate pacing pulses to be applied, through the optional switch 120 and the connector 110, to at least one of the connected cardiac leads and one or more electrodes of the cardiac leads.

The pulse generator 140 is connected to and controlled by a pulse generator controller 130, represented by a general controller 130 in FIG. 2. The pulse generator controller 130 controls the particular pacing pattern to be applied to the subject's heart. In a particular embodiment the pulse generator controller 130 is configured to control the pulse generator 140 to generate and apply pacing pulses to connected electrodes according to either a default pacing mode or an ischemic pacing mode. The pulse generator controller 130 is thereby configured to switch from the default or normal pacing mode to the ischemic pacing mode based on the ischemia detector 132 detecting an ischemic event.

The default pacing mode is the traditional pacing mode selected for the subject by the physician based on the particular cardiac disease of the subject. This means that the pulse generator controller 130 mainly operates according to this default pacing mode. However, in connection with a detected ischemic event as signaled by an ischemia signal generated by the ischemia detector 132 in response to the detection of an ischemic event, the pulse generator controller 130 switches to the ischemic pacing mode. The controller 130 could then include a dedicated mode selector 136 that is responsive to the ischemia signal and triggers a switch to the ischemic pacing mode based on the ischemia signal.

Compared to the default pacing mode, the ischemic pacing mode could provide a reduced load on the myocardium of the heart, for instance by reducing the maximum tracking rate or the rate response function used in the default pacing mode. Furthermore, or alternatively, the IMD 100 could be configured to be more sensitive to any arrhythmia events when operating in the ischemia pacing mode as compared to the default pacing mode. Generally, the IMD 100 comprises an intracardiac electrogram (IEGM) processor or circuit 160 connected to the connector 110 and configured to generate an IEGM signal based on electrical activity of the heart sensed by at least one electrode connected to the connector 110. The controller 130 could then process the IEGM signal to determine a current heart rate of the subject's heart.

Arrhythmia detection is traditionally performed by an IMD 100 if the current heart rate exceeds a predefined rate threshold. The IMD 100 could then use two different such rate thresholds, one rate threshold during the default pacing mode and another, typically lower rate threshold during the ischemic pacing mode.

The controller 130 advantageously switches back from the ischemic pacing mode to the default pacing mode after the end of the detected ischemic event. This switch back to the default pacing mode preferably occurs following a defined time period from when the ischemia detector 132 detects the end of the ischemic event, i.e. when the oxygen concentration in coronary sinus blood has, following the temporary decrease and increase, returned back to the normal concentration level. The length of this defined time period is preferably programmed into the IMD 100 by the subject's physician.

The IMD 100 as illustrated in FIG. 2 preferably comprises a ventricular sensing circuit 150 implemented in the IMD 100 to sense electrical activity in a ventricle using an electrode connected to the connector 110.

The IMD 100 may optionally also comprise a corresponding atrial pulse generator and an atrial sensing circuit (not shown in FIG. 2) if the connector 110 is connectable to at least one atrial cardiac lead. The ventricular and atrial pulse generators 140 of the IMD 100 may then include dedicated, independent pulse generators, multiplexed pulse generators, or shared pulse generators. The pulse generators 140 are controlled by the controller 130 via appropriate control signals, respectively, to trigger or inhibit the stimulating pulses.

The ventricular and optional atrial sensing circuits 150 of the IMD 100 may include dedicated sense amplifiers, multiplexed amplifiers, or shared amplifiers. The electronic configuration switch 120 determines the "sensing polarity" of the cardiac signal by selectively closing the appropriate switches, as is also known in the art. In this way, the physician may program the sensing polarity independent of the stimulation polarity. The sensing circuits are optionally capable of obtaining information indicative of tissue capture.

Each sensing circuit 150 preferably employs one or more low power, precision amplifiers with programmable gain and/or automatic gain control, band-pass filtering, and a threshold detection circuit, as known in the art, to selectively sense the cardiac signal of interest.

The outputs of the ventricular and optional atrial sensing circuits 150 are connected to the controller 130, which, in turn, is able to trigger or inhibit the ventricular and optional atrial pulse generators 140, respectively, in a demand fashion in response to the absence or presence of cardiac activity in the appropriate chambers of the heart.

The controller 130 of the IMD 100 is preferably in the form of a programmable microcontroller 130 that controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 130 is configured to process or monitor input signals as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

Furthermore, the controller 130 is also typically capable of analyzing information output from the sensing circuits 150 to determine or detect whether and to what degree tissue capture has occurred and to program a pulse, or pulse sequence, in response to such determinations. The sensing circuits 150, in turn, receive control signals over signal lines from the controller 130 for purposes of controlling the gain, threshold, polarization charge removal circuitry, and the timing of any blocking circuitry coupled to the inputs of the sensing circuits 150 as is known in the art.

The optional electronic configuration switch 120 includes a plurality of switches (not shown) for connecting the desired connector terminals 111-115 to the appropriate I/O circuits, thereby providing complete electrode programmability. Accordingly, the electronic configuration switch 120, in response to a control signal from the controller 130, determines the polarity of the stimulating pulses by selectively closing the appropriate combination of switches as is known in the art.

While a particular IMD 100 is shown in FIG. 2, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination.

The IMD 100 additionally includes a battery 180 that provides operating power to all of the circuits shown in FIG. 2.

Figure 6:
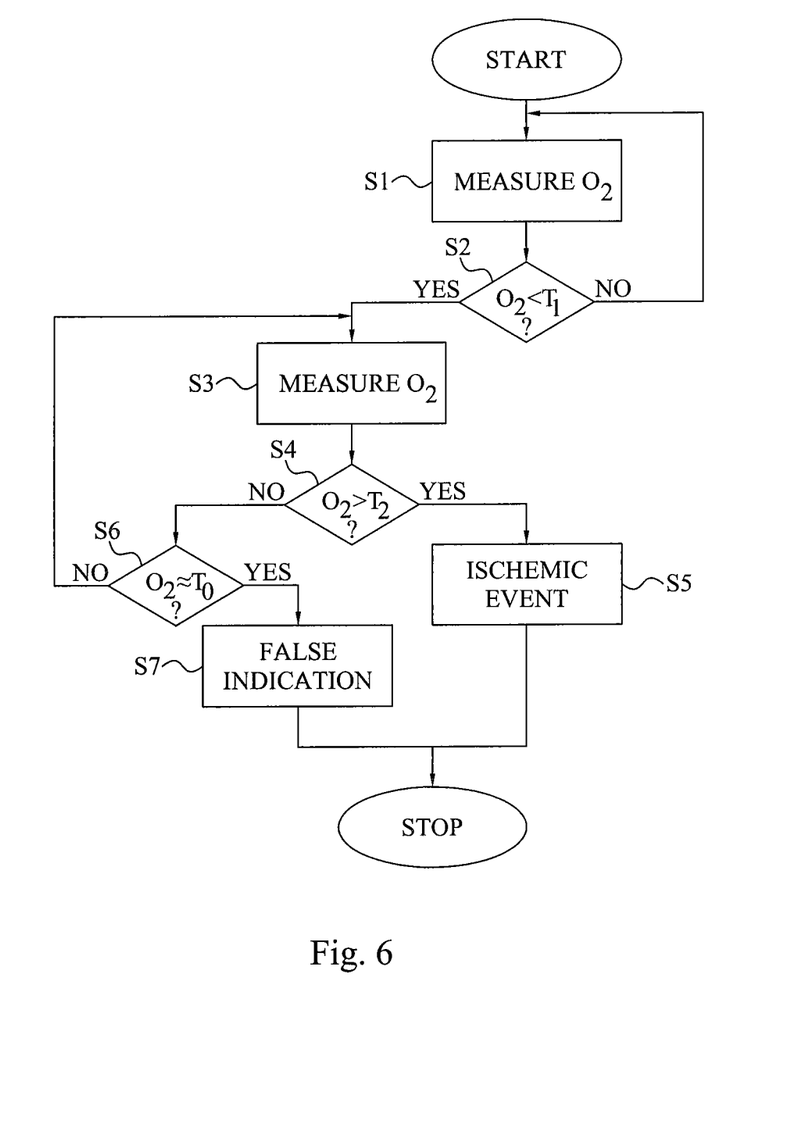
FIG. 6 is a flow diagram illustrating a method of detecting an ischemic event according to an embodiment.

FIG. 6 is a flow diagram illustrating a method of detecting an ischemic event in a heart of a subject. The method starts in step S1, where the oxygen concentration in coronary sinus blood of the heart is measured. In a next step S2, the measured oxygen concentration ($O_2$) is compared to a first threshold value ($T_1$). If the oxygen concentration in coronary sinus blood is not below the first threshold value the method returns to step S1 to continue the measurements. Hence, in this case the oxygen concentration is close to the baseline value representing normal oxygen concentration in the coronary sinus blood.

However, if the measured oxygen concentration is below the first threshold value the method continues to step S3 where further oxygen concentration measurements are performed. Such a further measured oxygen concentration is then compared in step S4 to a second threshold value ($T_2$). If the oxygen concentration exceeds this second threshold value an ischemic event is detected in step S5 since the oxygen concentration then initially drops below the baseline and then subsequently significantly increases above the baseline, see FIG. 4.

If the measured oxygen concentration does not exceed the second threshold value in step S4 the method continues to step S6, where the oxygen concentration is compared to the normal oxygen concentration value ($T_0$). If the oxygen concentration is substantially equal to this normal oxygen concentration value, a non-ischemic event is detected corresponding to a false ischemic indication in step S7. Otherwise the method continues from step S6 to step S3.

In particular embodiments, the comparisons performed in steps S2, S4 and S6 between a measured oxygen concentration and a threshold value is preferably performed by comparing an average oxygen concentration calculated for a predefined time period or for a predefined number of consecutive measurement samples. Alternatively, the comparison is performed multiple times for a predefined number of consecutive measurement samples. The decision whether the oxygen concentration is below or exceeds the particular threshold value is then only taken once all or a defined minimum number of these consecutive measurement samples is below or exceeds the threshold.

Both these techniques, i.e. averaging or using multiple samples, combats noise in the sensor signal and any odd measurement value that otherwise could lead to an incorrect detection.

In a general aspect of the embodiments, the method comprises measuring oxygen concentration in coronary sinus blood of the heart and detecting an ischemic event if the oxygen concentration in the coronary sinus temporarily decreased below a normal oxygen concentration in coronary sinus blood for a non-ischemic status of the heart and followed by an increase in oxygen concentration in the coronary sinus blood above the normal oxygen concentration.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable medical device comprising:
    an implantable oxygen sensor configured to generate a sensor signal representative of oxygen concentration in coronary sinus blood of a heart;
    memory to store a normal oxygen concentration threshold of blood in the coronary sinus; and
    an ischemia detector coupled to said oxygen sensor and configured to process said sensor signal received from said implantable oxygen sensor, wherein said ischemia detector is configured to determine if an ischemic event occurs in said heart if said sensor signal indicates a temporary decrease in oxygen concentration in said coronary sinus blood below the normal oxygen concentration threshold in coronary sinus blood for a non-ischemic status of said heart followed by temporary increase in oxygen concentration in said coronary sinus blood above the normal oxygen concentration in the coronary sinus blood for a non-ischemic status of said heart, further followed by an oxygen concentration in the coronary sinus blood that is substantially equal to said normal oxygen concentration threshold.

2. The implantable medical device according to claim 1, wherein said ischemia detector is configured to determine if an ischemic event occurs if said sensor signal indicates the temporary decrease in said oxygen concentration in said coronary sinus blood below said normal oxygen concentration threshold for about 3-5 minutes followed by the temporary increase in oxygen concentration in said coronary sinus blood above said normal oxygen concentration for 1-5 minutes.

3. The implantable medical device according to claim 1 further comprising
    a message generator configured to generate, in response to said ischemia detector determining that an ischemic event has occurred, a notification message comprising a notification of said detected ischemic event; and
    a transmitter configured to wirelessly transmit said notification message to a non-implantable device.

4. The implantable medical device according to claim 1 further comprising an implantable medical lead comprising at least one pacing electrode, wherein said implantable medical device further comprises:
    a pulse generator connected to said implantable medical lead and configured to generate pacing pulses to be applied to said at least one pacing electrode; and
    a pulse generator controller connected to said pulse generator and configured to control said pulse generator to apply pacing pulses to said at least one pacing electrode according to a default pacing mode or an ischemic pacing mode, wherein said pulse generator controller is configured to switch from said default pacing mode to said ischemic pacing mode based on said ischemia detector determining that an said ischemic event has occurred.

5. The implantable medical device according to claim 1, wherein said implantable oxygen sensor is selected from an implantable partial oxygen pressure, $pO_2$, sensor and an implantable oxygen saturation, $SO_2$, sensor.

6. The implantable medical device according to claim 1 wherein said ischemia detector is configured to generate an ischemia detection notification if said sensor signal indicates a temporary decrease in oxygen concentration in said coronary sinus blood below said normal oxygen concentration in coronary sinus blood for said non-ischemic status of said heart followed by said increase in oxygen concentration in said coronary sinus blood above said normal oxygen concentration, said implantable medical device further comprising a memory configured to store said ischemia detection notification.

7. An implantable medical device comprising:
   an implantable oxygen sensor configured to generate a sensor signal representative of oxygen concentration in coronary sinus blood of a heart;
   memory to store a normal oxygen concentration threshold of blood in the coronary sinus; and
   an ischemia detector coupled to said oxygen sensor and configured to process said sensor signal received from said implantable oxygen sensor, wherein said ischemia detector is configured to determine if false ischemic event representing a non-ischemic status of said heart if said sensor signal indicates said temporary decrease in oxygen concentration in said coronary sinus blood below said normal oxygen concentration threshold followed by an increase in oxygen concentration in said coronary sinus blood up to but not above said normal oxygen concentration threshold.

8. A method for detecting ischemia in a heart of a subject, said method comprising:
   measuring oxygen concentration in coronary sinus blood of said heart; and
   determining if an occurrence of an ischemic event has occurred in the heart if said oxygen concentration in said coronary sinus blood temporarily decreases below a normal oxygen concentration in coronary sinus blood for a non-ischemic status of said heart followed by a temporary increase in oxygen concentration in said coronary sinus blood above the normal oxygen concentration in coronary sinus blood for a non-ischemic status of said heart, further followed by an oxygen concentration in the coronary sinus blood that is less than or equal to said normal oxygen concentration.

9. The method according to claim 8 wherein determining if an ischemic event has occurred comprises determining if an ischemic event has occurred if the temporary decrease in said oxygen concentration in said coronary sinus blood decreases below said normal oxygen concentration for no more than 3-5 minutes followed by the temporary increase in oxygen concentration in said coronary sinus blood above said normal oxygen concentration for 1-5 minutes.

* * * * *